United States Patent [19]
Weinshenker

[11] 3,940,438
[45] Feb. 24, 1976

[54] CRYSTALLINE RACEMIC 9α,11α,15(S)-TRIHYDROXY-5-CIS,13-TRANS-PROSTADIENOIC ACID

[75] Inventor: Ned M. Weinshenker, Palo Alto, Calif.

[73] Assignee: Alza Corporation, Palo Alto, Calif.

[22] Filed: Sept. 21, 1973

[21] Appl. No.: 399,591

Related U.S. Application Data

[63] Continuation of Ser. No. 146,491, May 24, 1971, abandoned.

[52] U.S. Cl. .............................. 260/514 D; 424/317
[51] Int. Cl.² ......................................... C07C 61/38
[58] Field of Search .............................. 260/514 D

[56] References Cited
FOREIGN PATENTS OR APPLICATIONS
2,011,969    8/1970    Germany ........................... 260/468

OTHER PUBLICATIONS

Corey et al., TACS 91, 5675 (1969).

*Primary Examiner*—Robert Gersh
*Attorney, Agent, or Firm*—Paul L. Sabatine; Edward L. Mandell

[57] ABSTRACT

The invention concerns a novel crystalline racemate, 9α,11α,15(S)-trihydroxy-5-cis,13-trans-prostadienoic acid. The racemate can be administered in pharmaceutical dosage forms or from a drug delivery device at a programmed rate for producing smooth muscle stimulation, termination of pregnancy, induction of labor or induction of menses.

1 Claim, 9 Drawing Figures

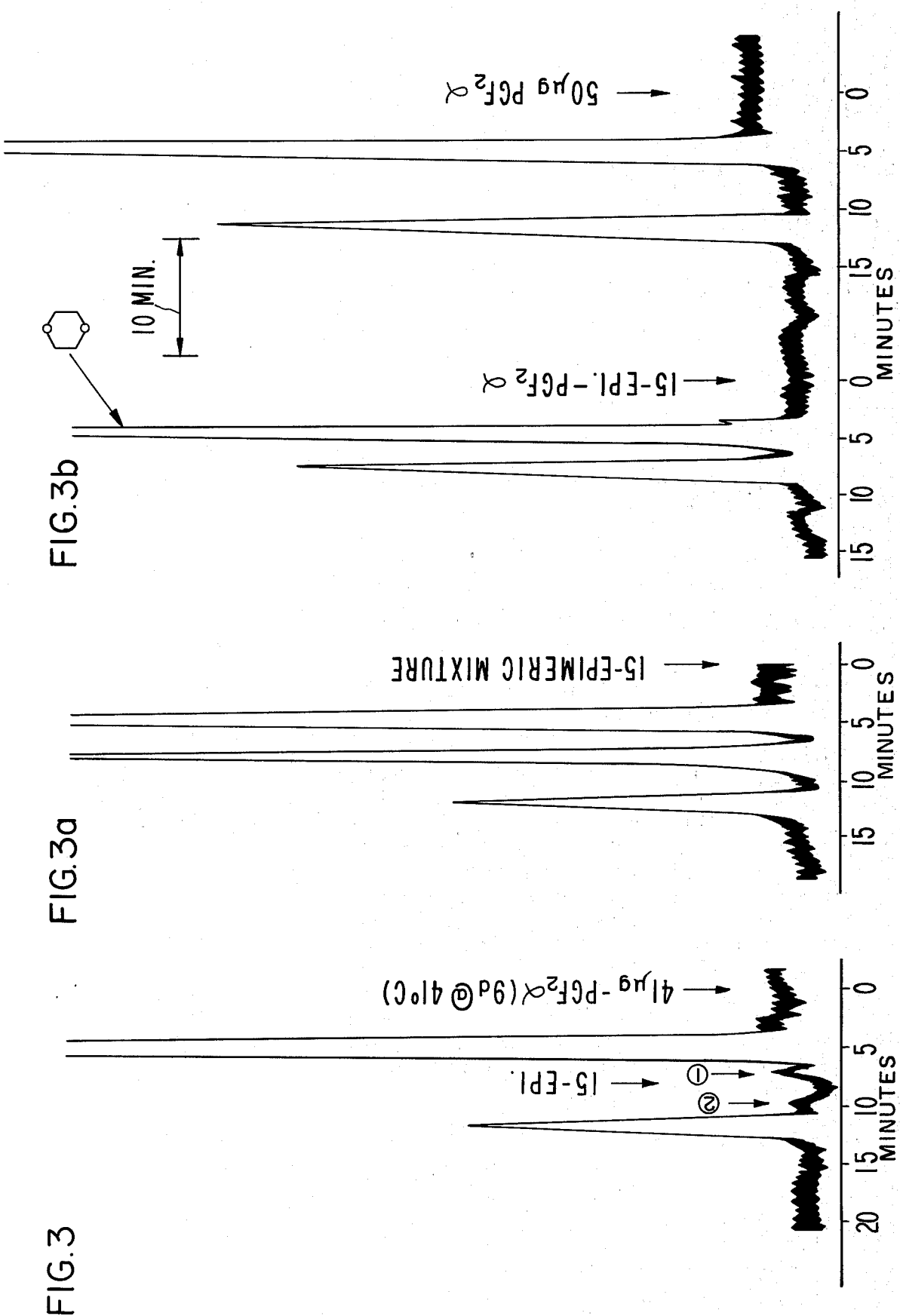

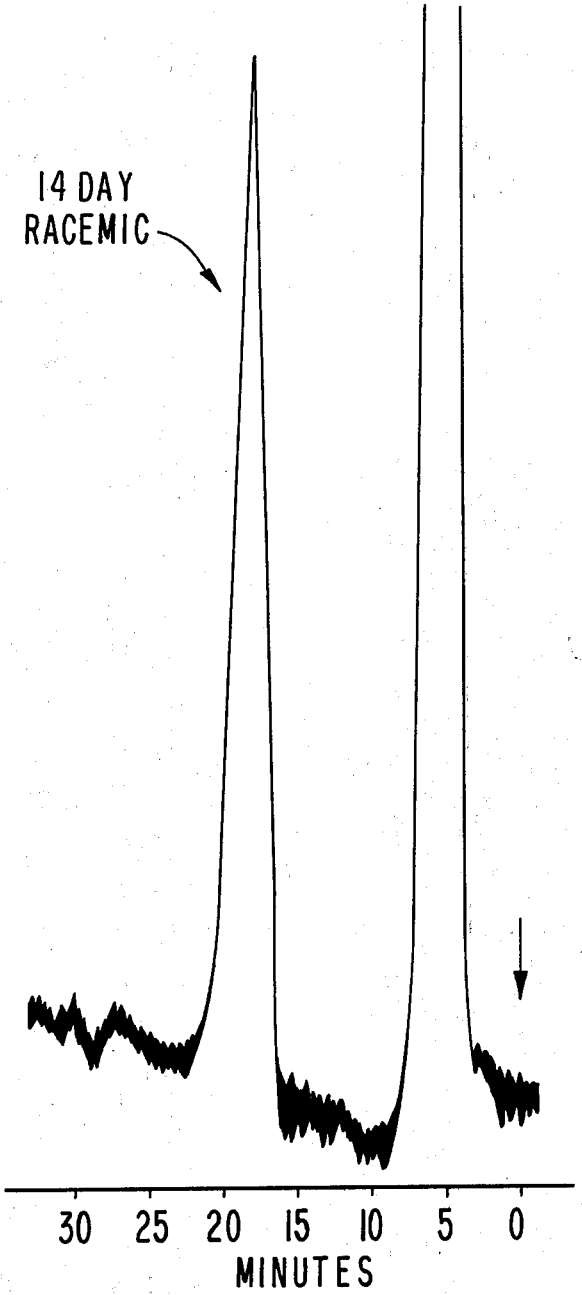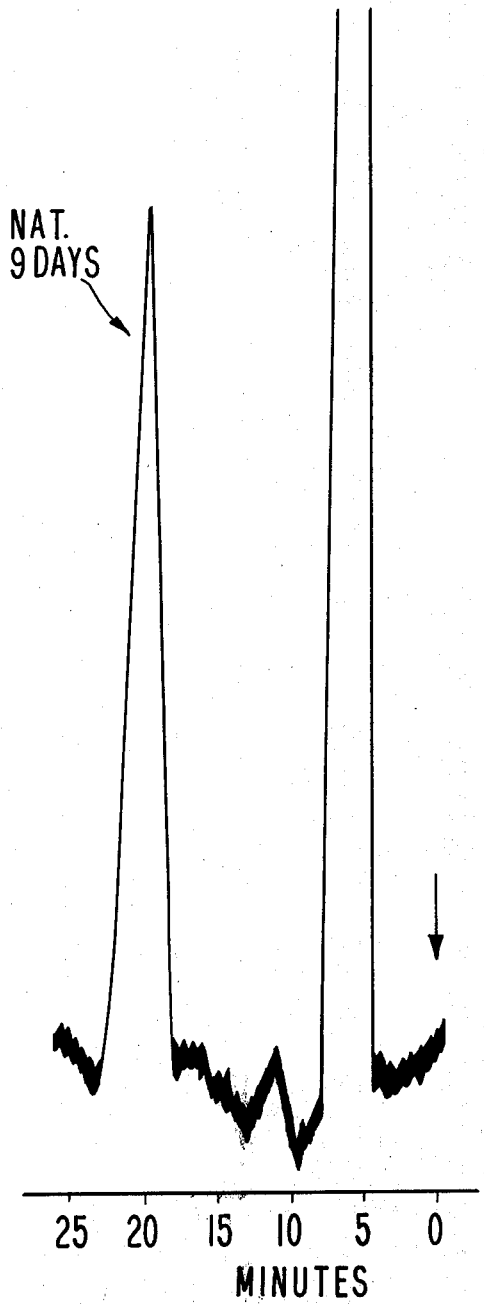

CRYSTALLINE RACEMIC 9α,11α,15(S)-TRIHYDROXY-5-CIS,13-TRANS-PROSTADIENOIC ACID

REFERENCE TO RELATED APPLICATION

This application is a continuation of my copending U.S. patent application Ser. No. 146,491 filed on May 24, 1971 now abandoned, with complete application of said application incorporated into this application by reference.

BACKGROUND OF THE INVENTION

1. Field of the Invention

This invention relates to a new and useful polymorph, and more particularly it pertains to a novel polymorph, crystalline racemic 9α,11α15(S)-trihydroxy-5-cis,13-transprostadienoic acid.

2. Description of the Prior Art

Racemic 9α,11α,15(S)-trihydroxy-5-cis,13-trans-prostadienoic acid, also known as dl-prostaglandin $PGF_{2\alpha}$, is a recently synthesized, colorless, oily racemate, J. Am. Chem. Soc., Vol. 91, pages 5675 to 5677, 1969 and Chem. Comm., No. 6, pages 304 to 305, 1969, that possesses valuable, therapeutic properties. The properties broadly include the ability to modify smooth muscle activity, the termination of pregnancy, induction of labor, and induction of menses. Prostaglandins, Progress in the Chemistry of Fats and Other Lipids, Vol. IX, Part 2, pages 231 to 278, 1968, Pergamon Press, Inc.

While the above mentioned therapeutic properties of the oily racemate are known to the prior art through 9α,11α,15(S)-trihydroxy-5-cis,13-trans-prostadienoic acid, [$PGF_{2\alpha}$], the art apparently never used the oily racemate because it would encounter problems in its attempts to obtain and to use the oily racemate for therapeutic purposes. For example, typical problems that would be encountered by the art include the difficulty to obtain and to keep essentaily pure racemic $PGF_{2\alpha}$ because the oily racemate would decompose during its distillation and also because it would readily oxidize during storage to presently unidentified products that lack prostaglandin utility. Another problem that would be encountered with the oily racemate would arise in using the oily racemate in conventional pharmaceutical dosage forms and in drug delivery devices. In the pharmaceutical forms, the oily racemate would undergo air oxidation and leakage therefrom. In the drug delivery devices comprising a rate release membrane containing the oily racemate, there would be uncontrolled passage of the oily racemate from the rate release membrane to essentially prevent its administration at a programmed rate over a predetermined time period to produce a therapeutic effect. Thus, in view of the foregoing discussion, it can readily be seen that the art critically needs a novel and useful form of the racemic 9α,11α,15(S)-trihydroxy-5-cis,13-trans-prostadienoic acid that possesses improved drug stability and can advantageously be used in pharmaceutical dosage forms or in drug delivery devices for its outstanding therapeutic properties.

OBJECTS OF THE INVENTION

Accordingly, it is an object of the present invention to provide a novel form of racemic 9α,11α,15(S)-trihydroxy-5-cis, 13-trans-prostadienoic acid [crystalline racemic $PGF_{2\alpha}$] that can be used by the pharmaceutical art for obtaining its therapeutic effects.

It is another object of the present invention to provide a novel and useful racemate of 9α,11α,15(S)-trihydroxy-5-cis,13-trans-prostadienoic acid that essentially overcomes the problems encountered by the prior art.

Still a further object of the invention is to provide a new polymorph of racemic 9α,11α,15(S)-trihydroxy-5-cis,13-transprostadienoic acid [crystalline racemix $PGF_{2\alpha}$] that can be administered in conventional pharmaceutical formulations or from drug delivery devices.

Still yet a further object of the invention is to provide a new crystalline racemate, 9α,11α,15(S)-trihydroxy-5-cis,13-trans-prostadienoic acid [crystalline racemic $PGF_{2\alpha}$] that can be obtained from the prior art oily racemate and which new crystalline form can be obtained with a high degree of purity, by conventional, recrytallization, purification techniques.

Yet a further object of the invention is to make available to the art a new, crystalline racemate, 9α,11α,15(S)-trihydroxy-5-cis,13-trans-prostadienoic acid [crystalline racemic $PGF_{2\alpha}$] that possesses both enhanced stability and shelf life and can be characterized by reliable data.

Still a further object of the invention is to make available the racemate 9α,11α,15(S)-trihydroxy-5-cis,13-trans-prostadienoic acid in solid, crystalline form having improved stability and essentially free from autoxidation.

Yet still a further object of the invention is to provide crytalline racemic 9α,11α,15(S)-trihydroxy-5-cis,13-transprostadienoic acid that possesses increased shelf life for storage at room temperature substantially free of air oxidation and degradation.

Still a further purpose of the invention is to provide a solid crystal racemate 9α,11α,15(S)-trihydroxy-5-cis,13-transprostadienoic acid capable of definition by means of interplanar spacing.

Yet a further object of the invention is to provide crystalline racemic 9α,11α,15(S)-trihydroxy-5-cis,13-trans-prostadienoic acid that can be formulated and compounded into pharmaceutical formulations essentially free of the disadvantages known to the prior art.

These and other objects, as well as features and advantages of the invention will be readily apparent to those skilled in the art upon a reading of the present disclosure and the accompanying claims.

SUMMARY OF THE INVENTION

The invention concerns a new polymorph, crystalline, racemic 9α,11α15(S)-trihydroxy-5-cis,13-trans-prostadienoic acid, [crystalline racemic $PGF_{2\alpha}$]. The new solid polymorph possesses unexpected stability and it also possesses the therapeutic utility of 9α,11α,15(S)-trihydroxy-5-cis,13-trans-prostadienoic acid, [$PGF_{2\alpha}$]. Additionally, it can be administered in stable conventional, pharmaceutical dosage formulations or from drug delivery devices.

DETAILED DESCRIPTION OF THE INVENTION

Figure 1:
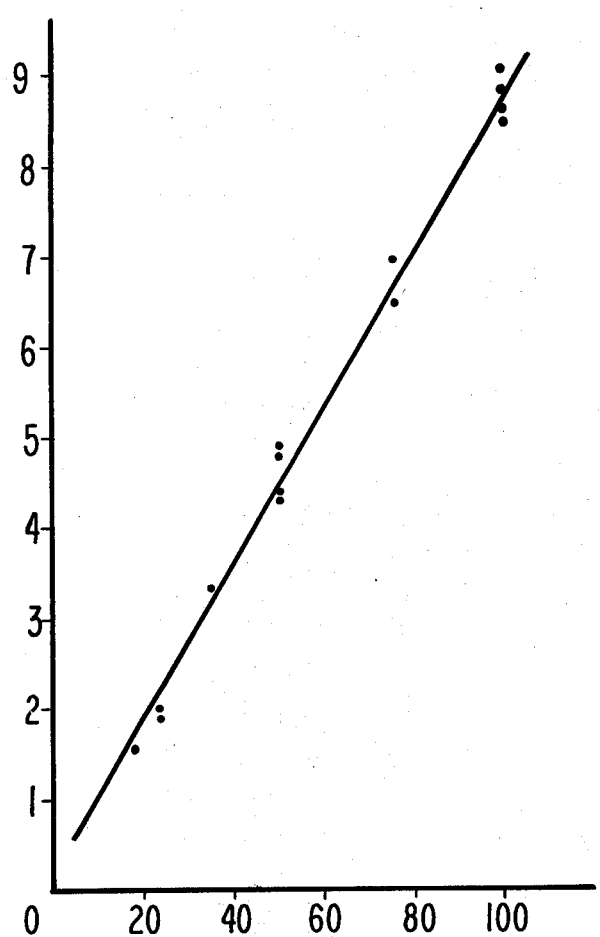

In attaining the objects and advantages of this invention, it has now been unexpectedly found that a new solid crystalline racemate, 9α,11α,15(S)-trihydroxy-5-cis,13-trans-prostadienoic acid, [crystalline racemic $PGF_{2\alpha}$], hereinafter designated as polymorph II, can be made available to the art to essentailly overcome the difficulties associated with the prior art oily racemate of 9α,11α,15(S)-trihydroxy-5-cis,13-trans-prostadienoic acid [oily racemic $PGF_{2\alpha}$], hereinafter designated as polymorph I. It has further been unexpectedly found that polymorph II of the invention can be obtained from polymorph I by the direct conversion of the oily racemate to the crystalline racemate, and also by first dissolving polymorph I in a solvent such as acetonitrile, dioxane, tetrahydrofuran, etc., followed by either seeding or by dissolution and seeding to give polymorph II. Additionally, the invention also provides purified polymorph II, as the purification of polymorph II can be achieved by conventional, easily repeated crystallization techniques from standard solvent medium, such as acetonitrile, tetrahydrofuran, dioxane, benzene, furan and the like, where heretobefore for obtaining polymorph I, laborious techniques such as chromatographic, counter current distribution and the like purification procedures were required since the oily racemate is not stable during distillation, and because it easily oxidizes under ambient conditions. Additionally, the isolation and recovery of polymorph II is easier to expedite because polymorph II is freed more readily from the volatile solvents used during the purification procedures than is polymorph I.

The polymorph II of the present invention can be distinguished from the oily polymorph I, which readily undergoes air oxidation by its greater stability and increased shelf life and by its interplanar spacings as shown by X-ray powder diffraction as set forth in Table I.

TABLE 1

X-RAY DIFFRACTION DATA

| Polymorph II | | Polymorph I |
|---|---|---|
| Interplanar Spacings, A° | Estimated Intensity Strongest Line = 10 | |
| 27.90 | 7 | |
| 18.19 | 1 | |
| 13.00 | 3 | Oily |
| 10.32 | 3 | |
| 8.38 | 9 | |
| 7.31 | 5 | |
| 6.06 | 6 | |
| 5.40 | 5 | |
| 4.92 | 9 | |
| 4.67 | 8 | |
| 4.45 | 8 | |
| 4.09 | 10 | |
| 3.54 | 3 | |
| 3.30 | 3 | |
| 2.98 | 3 | |
| 2.79 | 3 | |
| 2.63 | 1 | |
| 2.53 | 3 | |
| 2.04 | 3 | |

The physical crystalline phase data, as set forth in Table II, further serves to characterize completely polymorph II.

TABLE II

| Crystal System | Monoclinic |
|---|---|
| Crystal Habit | Tubular |
| Optic Sign | Negative |
| Melting Point | 63.5°C – 64°C |

Illustratively, polymorph II of the present invention can be prepared according to the following examples.

EXAMPLE A

Preparation of Polymorph II. First, 150.5 mg of racemic 11,15-bis(tetrahydropyranyl)ether of 9α,1-1α,15(S)-trihydroxy-5-cis,13-trans-prostadienoic acid, [rac. 11,15-bis-THP of $PGF_{2\alpha}$], prepared according to the processes reported in J. Am. Chem. Soc., Vol 91, pages 5675 to 5677, 1969; and, ibid, Vol 92, pages 2586 to 2587, 1970 was dissolved in 0.4 ml of tetrahydrofuran with gentle stirring and then, 4 ml of a 65 to 35 solution of acetic acid to water was added and the mixture stirred at 40° to 45°C for about 4 hours. Next, the volatiles were removed under vacuum (<0.1 mm Hg), and the residue containing the prostaglandin was chromatographed on a column containing about 4 gm of acidic silica, commercially available as SilicAR$^{(R)}$, CC-4, 100–200 mesh, from the Mallinckrodt Chemical Works. The prostaglandin was eluted with approximately 4 column volumes of an eluant consisting of a 2 to 1 mixture of cyclohexane and ethylacetate, with 15 to 20 ml fractions collected therefrom. In fraction 7, there appeared an oily, impure fraction of racemic $PGF_{2\alpha}$, followed by fractions of pure racemic $PGF_{2\alpha}$ in fractions 8 to 12. Fractions 8 to 12 were combined to yield 60 mg of pure, oily racemic $PGF_{2\alpha}$ which slowly crystallized under ambient conditions to directly yield polymorph II, or crystalline racemic $PGF_{2\alpha}$, with a melting point of 63.5°C to 64°C.

EXAMPLE B

The procedure used in Example A for preparing polymorph II was followed in this example, and, all the conditions were substantially as previously described except for the use of solvent and seeding changes in the procedure as now set forth. In this example 571 mg of racemic 11,15-bis(tetrahydropyranyl)ether of 9α,1-1α15(S)-trihydroxy-5-cis,13-trans-prostadienoic acid [rac. of 11,15-bis-THP of $PGF_{2\alpha}$], was dissolved in 4 ml of tetrahydrofuran and 30 ml of 65:35 acetic acid:- water mixture. The mixture was heated at 56°C for 3½ hrs, cooled to room temperature and stripped in vacuo. Next, the residue was chromotographed on a 6 gm SilicAR, CC-4 column with a 1:1 cyclohexane:ethylacetate eluant for fractions 1 to 5 and ethyl acetate eluant was used for fractions 6 through 12. Fractions 7 to 12 contained the racemic, pure, oily $PGF_{2\alpha}$ and they were combined and concentrated to yield about 135 mg of the oily racemate. Next, the oily racemate was dissolved in the solvent, acetonitrile, cooled, and on scratching gave crystals, that are characterized as polymorph II, or crystalline racemic $PGF_{2\alpha}$. The product, polymorph II, can be further purified, if needed, by repeated dissolution and seeding from an organic solvent such as acetonitrile, furan, etc., to yield pure, crystalline racemic $PGF_{2\alpha}$, or polymorph II.

EXAMPLE C

Natural 9α,11α,15(S)-trihydroxy-5-cis,13-trans-prostadienoic acid, natural $PGF_{2\alpha}$, prepared from total synthesis was a soft, waxy semi-crystalline compound melting in the range of 25°–32°. A weighed sample was diluted with dioxane to produce a solution which was 10μg $PGF_{2\alpha}$/μl of solution. This solution was used to calibrate the response of the differential refractometer of a Waters Assoc. Model 100 high pressure liquid chromatograph (h.p.l.c.). The calibration appears in FIG. 1. FIG. 1, the $PGF_{2\alpha}$ peak height conditions are as follows: column 4 feet ×0.125 inches o.d., column of Corasil -II. Solvent 0.2% HOAc/EtOAc wherein the former is acetic acid and the latter is ethyl acetate. Flow 0.9ml/min. Reaction times: dioxane front appears at 30 min. $PGF_{2\alpha}$ at 14 min. from injection corresponding to column void volume after void volume displacement. The numbers on the x-axis are μg injected and the numbers along the y-axis indicate detector response in inches at peak heights.

Figure 2:
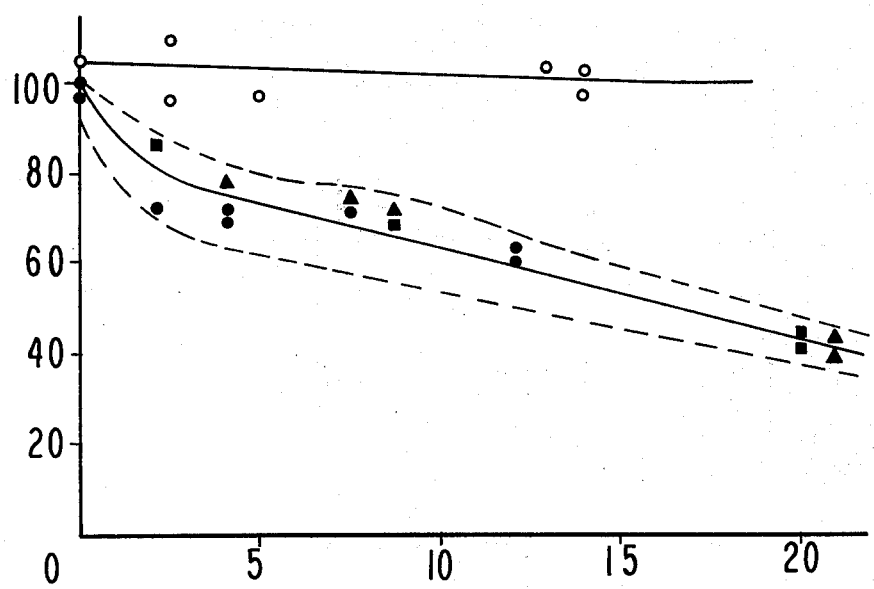

Weighed samples, 0.5–1.0 mg. ± 0.03 mg, of $PGF_{2\alpha}$ and crystalline racemic $PGF_{2\alpha}$ were placed in 1 dram vials. These vials were randomly divided between storage at −20°C under argon and storage at 41 ± 2°, open to the air, in a sand bath. At stipulated times samples were removed from both types of storage, diluted to 10μg $PGF_{2\alpha}$ /μl, and assayed by h.p.l.c. The −20° storage samples always assayed within experimental error of fresh standards (±6%). Individual assays of 41°C stored samples are collected in FIG. 2. In FIG. 2, the loss of $PGF_{2\alpha}$ on storage open to air at 41 ± 2°C is set forth. The open symbols are for racemic $PGF_{2\alpha}$ and the closed symbols are for nat. $PGF_{2\alpha}$. The different symbols are used to indicate different samples. Replicate analysis appear as multiple used of the same symbols at any one time. Further description of FIG. 2 indicates the percent of $PGF_{2\alpha}$ remaining. The numbers along the x-axis are days at 41 ± 2°C and along the y-axis are percents. The crystalline racemate assayed 103 ± 3% based on the natural compound. In the light of these studies and the customary precautions taken in the storage of the natural compound relative to the racemate, the results indicate superior long term storage stability for the racemic crystals II.

The oily $PGF_{2\alpha}$ degrades by oxidation rapidly at first suggestive of a surface reaction, and then more slowly with a measured half life of 17 days. The crystalline racemate is unchanged after 14 days. The racemate change as measured by $PGF_{2\alpha}$ is 3% (±~4~6%). This is an unexpected and superior contribution for the prostaglandin of the invention. Since, prostaglandins, including the dienoics, are known to be unstable, as they undergo autoxidation on exposure to air. *Methods of Biochemical Analysis, Vol.* 17, pages 325 to 371, 1969, published by Interscience Publishers, New York.

Figure 4B:
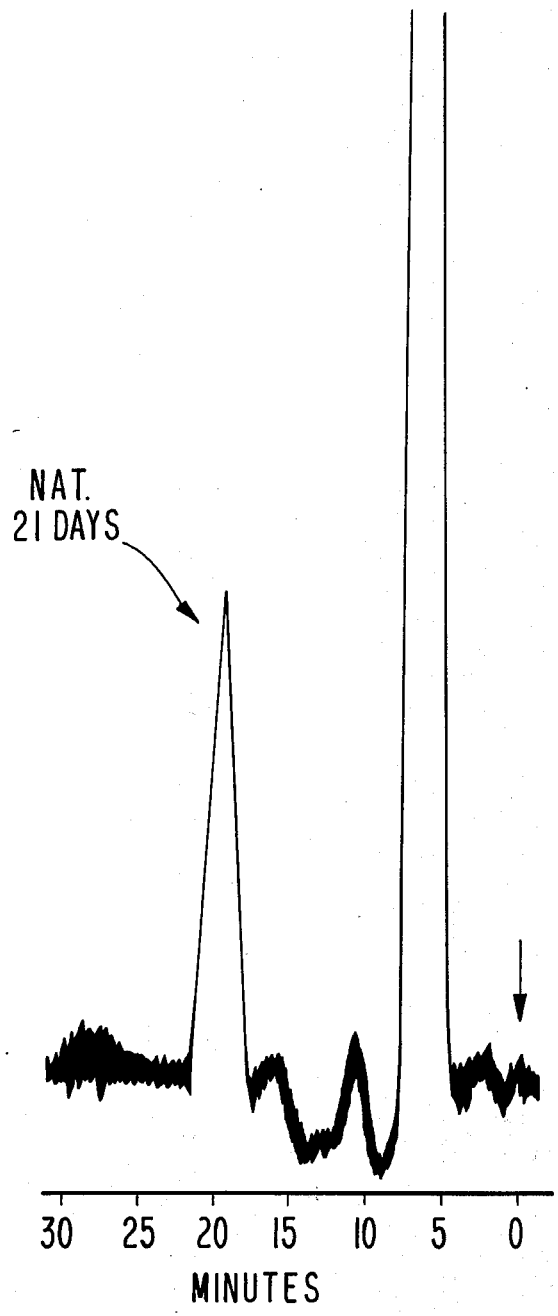
Figure 4C:
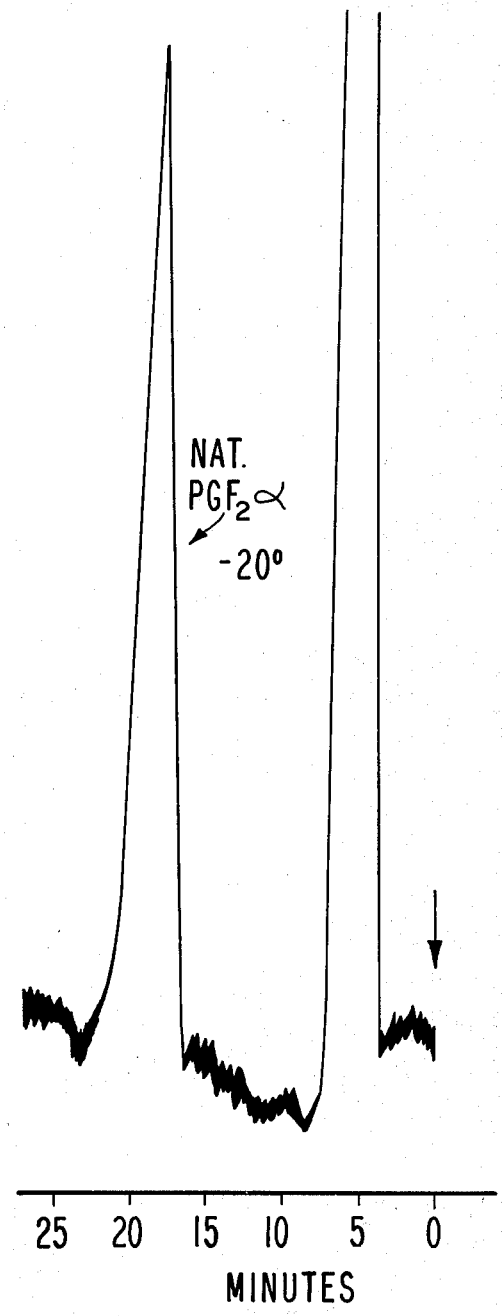

FIGS. 3, 3a and 3b show the traces from rapid analysis, (at 1 ml/min.). The figures also show the separation of $PGF_{2\alpha}$ and its 15-epimer. Neither of the degradation products seen in the $PGF_{2\alpha}$ sample stored 9 days at 41° C corresponds to 15-epi-$PGF_{2\alpha}$. FIG. 4 shows traces from analysis run at lower flow rates, (~0.7 ml/min.). In FIGS. 4, 4a and 4b, all injections represent 100 μg of $PGF_{2\alpha}$ initial samples. The unexpected nature of stable, crystalline polymorph II was also seen in samples kept at 25°C with constant exposure to the air without any evidence of crystalline loss after more than one year; while an oily racemic product would be over half oxidized in 17 days and evidence a continual oxidation loss with corresponding continual half-life losses.

Polymorph II of the invention can be used by the pharmaceutical art in a variety of pharmaceutical preparations for its therapeutic use. For example, polymorph II can be formulated for its therapeutic use. For example, polymorph II can be formulated into stable tablets, capsules, elixers, syrups, ointments, powders, creams, lotions, drops, pastes, jellies, injectable preparations, dispersions, food premix, and the like. The stable polymorph II can be administered by conveniently mixing it with non-toxic, pharmaceutically acceptable organic or inorganic carriers, such as gelatin, lactose, starches, talc, magnesium stearate and other conventionally employed pharmaceutically acceptable carriers. The parmaceutical preparation containing polymorph II may also include non-toxic auxiliary substances such as emulsifying, preserving, wetting agents and the like.

Exemplary of a typical method for preparing a tablet containing polymorph II is to first comminute polymorph II with a diluent such as starch, sucrose, kaolin or the like to form a mixture. Next, the mixture can be granulated with a binder such as gelatin, acacia mucilate, corn syrup and the like and, after mixing, the composition is screened to any predetermined particle sieve size. As an alternative, if preferred, to granulation, the just prepared mixture can be slugged through conventional tablet machines and the slugs comminuted before fabrication of the tablets. The freshly prepared tablets can be coated or they can be left uncoated and maintain their stability and strength, which was impossible with the unstable prior art oily prostaglandins. Representative of suitable coatings are the non-toxic coatings including shellac, methylcellulose, carnauba wax, styrene-maleic acid copolymers, and the like. For oral administration, compressed, shelf-storable tablets containing 0.01 microgram, 10 micrograms, 50 micrograms, 5 milligrams, to 250 milligrams and the like of polymorph II are manufactured in the light of the above disclosure and by fabrication techiques well known to the art as set forth in *Remington's Pharmaceutical Science*, Chapter 39, Mack Publishing Co., 1965. A typical storable and operable formulation for a tablet containing polymorph II as the active ingredient in a tablet is described in Example D.

EXAMPLE D

| | Per Tablet, mg |
|---|---|
| Polymorph II | 2.0 |
| Corn Starch | 15.0 |
| Corn Starch Paste | 4.5 |
| Lactose | 82.0 |
| Calcium Stearate | 2.0 |
| Dicalcium Phosphate | 50.0 |

To formulate the tablet, uniformly blend polymorph II, the corn starch, lactose and dicalcium phosphate in a standard v-blender until all the ingredients are uniformly mixed together. Next, the corn starch is prepared as a 10% syrup paste, and it is blended with the first prepared uniform mixture until a second uniform mixture is obtained. Then, the granulation is passed through a standard eight mesh screen, dried and re-screened with a twelve mesh screen. The dry granules are next blended with calcium stearate and compressed into tablets. Other tablets containing 0.05, 0.25, 1.0, 5.0, 10.0, 15,0 mgs. etc., are prepared in a like fashion. Another representative, essentially stable pharmaceutical composition prepared according to the spirit of the invention is set forth in Example E.

EXAMPLE E

A pharmaceutical composition comprising from 0.01 micrograms to 250 milligrams of crystalline, racemate 9α,11α,-15(S)-trihydroxy-5-cis,13-trans-prostadienoic acid wherein the crystals are characterized by the following X-ray diffraction data:

| Interplanar Spacings, A° | |
|---|---|
| 27.60 | 4.65 |
| 18.19 | 4.09 |
| 13.00 | 3.54 |

-continued
Interplanar Spacings, A°

| | |
|---|---|
| 10.33 | 3.30 |
| 8.38 | 2.98 |
| 7.31 | 2.79 |
| 6.06 | 2.63 |
| 5.40 | 2.53 |
| 4.92 | 2.04 |
| 4.67 | | and wherein the crystals system is monoclinic, the crystal habit is tubular, the optic sign is negative, and the melting point is 63.5°C to 64°C, mixed with a pharmaceutical carrier.

The manufacture of pharmaceutical capsules for oral use consists essentially of mixing polymorph II with a non-toxic carrier and enclosing the mixture in a gelatin sheath. The capsules can be in the art known soft form of a capsule made by enclosing polymorph II, or the capsule can be a hard capsule consisting essentially of polymorph II mixed with a nontoxic solid, such as talc, calcium stearate, calcium carbonate or the like. A typical capsule formulation is described in Example F.

EXAMPLE F

Capsules containing 0.1 mg, 0.5 mg, 2.5 mg, 10 mg, 20 mg, 25 mg, and the like of polymorph II are prepared by blending the following:

| | Per Capsule, mg |
|---|---|
| Polymorph II | 5.0 |
| Lactose, U.S.P. | 300.0 |
| Starch | 130.0 |
| Magnesium Stearate | 4.5 |

The blended ingredients are discharged into a commercially available capsule, and with the higher amounts of polymorph II as the active ingredient in the capsule, a suitable reduction is made in the amount of lactose. The formulation can be carried out under ambient conditions with conventional techniques.

Polymorph II can be incorporated into drug delivery devices comprising a member containing polymorph II or having polymorph II distributed therethrough for releasing polymorph II at a controlled rate for a predetermined period of time. The member containing polymorph II serves as a reservoir therefor, and it is usually shaped as a laminae, a film, or the like with at least one wall or part thereof made of a material suitable to the passage of polymorph II so that passage from the reservoir is a drug release rate governing process for effectively administering predetermined amounts of polymorph II for its ability to contract uterine myometrial muscle, induce parturition, interrupt early pregnancy and the like. The drug delivery devices suitable for the purpose of administering polymorph II are those devices that are readily inserted into body cavities, retained there and easily removed therefrom, devices that can be implanted and used as external drug delivery devices. Those skilled in the art can determine the rate of passage of polymorph II from or through materials by using standard in vivo and in vitro methods as reported in *Endocrinology*, Vol. 78, pages 208 to 211, 1966; *Encyl. Polymer Sci, Technol.*, Vol. 9, pages 794 to 807, 1968; *J. Pharm. Sci.*, Vol. 52, pages 1145 to 1149, 1963; *Circulation Research*, Vol. 10, pages 632 to 641, 1962; *J. of Chromatography*, Vol 44, pages 443 to 451, 1969; *J. Am. Chem. Soc.*, Vol. 91, pages 3398 to 3400, 1969; and, *European J. Biochem.*, Vol. 10, pages 411 to 418, 1969.

Polymeric materials suitable for use as a reservoir for administering polymorph II are materials of natural and synthetic materials include poly(propylene), poly(ethylene), poly(butadiene), poly(vinylchloride), poly(vinyllidene chloride), fluorinated ethylene-propylene copolymers, poly(ethylene terephthalate), poly(amides), poly(imides), poly(vinyl acetate), poly(vinyl pyrrolidone), poly(methyl vinyl ether maleic anhydride)copolymer, poly(methylmethacrylate), propylene vinyl butyrate copolymers, silicone rubbers poly(dimethylsiloxanes), silicone-carbonate copolymers, and the like. Exemplary of naturally occurring materials include cellulose ethers, agaragar, guar gum, gum tragacanth, casein, gelatine, and the like.

The manufacture of a drug delivery containing polymorph II is carried out by using standard techniques. For example, the reservoir can be formed by molding a polymeric material into the desired shape with polymorph II therein; or, the reservoir can be in the form of an envelope formed of films of polymeric material that releases polymorph II; or the reservoir can be in the form of an inert polymeric matrices with polymorph II dispersed therein. The standard techniques used for manufacturing the reservoir containing polymorph II include adding polymorph II to a liquid matrix material and then converting the matrix to a solid by curing, by immersion, coating, and the like. A typical drug delivery device containing polymorph II is described in Example G.

EXAMPLE G

A drug delivery device is prepared as follows: first, 3.2 g of solid polymorph II is thoroughly mixed with 23 g of medical grade polydimethylsiloxane elastomer and 5 g of the mixture aliquoted therefrom. Next, 1 to 2 drops of stannous octoate catalyst is added to the aliquote, the ingredients mixed, and then poured into an intravaginal rectangular mold formed of two parts. The mold's size and shape is variable and it is adapted for easy insertion, retention and removal from an animal's vagina. A typical mold's dimension generally corresponds to the dimension of the vaginal channel, that is, about 7 to 10 cm in length with a width of 5 to 30 mm for a mature mammal. Each part of the presently used mold is 5 mm by 70 mm to form a rectangle, 10 mm by 70 mm, and after filling, the parts are tightened to each other and the ingredients cure at 40°C to 50°C for 1 to 2 hours. The final cured product, or drug delivery device contains about 600 mg of polymorph II and placement of the device in the vaginal tract of mammals supplies an effective amount for the induction of labor.

EXAMPLE H

Other drug delivery devices are prepared as follows: a section of poly(vinylacetate) tubing having an outside diameter of 6 mm, an inside diameter of 4 mm and a length of about 15 mm, is filled with 150 mg of polymorph II and the ends of the tubing closed with plugs that are adhesively sealed thereto. The device can be subcutaneously implanted, or inserted into body openings for administering an effective amount of polymorph II. Another device can be prepared by mixing two equivalents of methylene isocynate, one equivalent of a polyethyl triol, one equivalent of 1,4-butanediol, and polymorph II and then polymerizing the mixture by standard methods to provide a poly(urethane)rubbertype drug delivery device. Likewise, other devices containing polymorph II which can permeate through polymeric substances such as poly(ethylene), nylon, etc., are prepared by techniques set forth in *Modern Plastic Encyclopedia*, Vol. 45, 1968, for providing controlled, continued, sustained, medication over desired predetermined periods of time.

The dose administered for polymorph II will of course vary for the chosen route of administration and the size of the recipient. The dose administered is not subject to definite bounds, but it will usually be an effective amount of polymorph II to achieve the biological function of the prostaglandin. Representative of a typical method for administering polymorph II is by the injectable-type administration route. By this route, from 0.2 micrograms to 10.0 micrograms per kilogram of body weight per minute by means of an infusion pump is useful for stimulating smooth muscle for inducing labor, for inducing menses and for termination of pregnancy. Polymorph II is administered from a drug delivery device intravaginally to primates, including mammals, at the rate of 20 mg to 50 mg every 2 hours for inducing parturition; and, from a drug delivery device intra-vaginally at the rate of 200 mg to 600 mg every 2 hours for the termination of pregnancy in primates, including mammals.

For administering to valuable domestic household, sport, or farm animals such as sheep, goats, cattle, etc., or to laboratory animals for scientific studies, polymorph II is administered in the form of a food premix, such as mixing with dried fish meal, oatmeal, straw, hay, ground corn, mash, and the like, and the prepared premix is added to the regular feed, thereby administering the compound to the domestic or laboratory animals in the form of feed.

In laboratory studies for determining the applicability of polymorph II to mammals, primates, avians and valuable animals, the studies are carried out with rats, guinea pigs, gerbils, mice, etc. For example, in laboratory studies with standard laboratory rats, polymorph II is administered orally by perfusion at the rate of 0.01 microgram to 1.0 microgram per minute for determining smooth muscle effects, and the like.

The above disclosure and examples are set forth for illustrating the mode and the manner of the invention. It is evident from the disclosure that the invention provides a new and useful product with improved stability. Also, the invention provides pharmaceutical compositions that can be made for present and future use with known and measurable activity that was not possible heretofore. Also, various modifications and embodiments can be made by those skilled in the art in the light of the invention without departing from the spirit of the invention.

I claim:

1. Crystalline, racemate $9\alpha,11\alpha,15(S)$-trihydroxy-5-cis,-13-trans-prostadienoic acid wherein the crystals are characterized by the following X-ray diffraction data:

| Interplanar Spacings, A° | |
|---|---|
| 27.60 | 4.65 |
| 18.19 | 4.09 |
| 13.00 | 3.54 |
| 10.33 | 3.30 |
| 8.38 | 2.98 |
| 7.31 | 2.79 |
| 6.06 | 2.63 |
| 5.40 | 2.53 |
| 4.92 | 2.04 |
| 4.67 | | and wherein the crystals system is monoclinic, the crystal habit is tubular, the optic sign is negative, and the melting point is 63.5°C to 64°C.

* * * * *